(12) United States Patent
Zimmer et al.

(10) Patent No.: US 7,826,898 B2
(45) Date of Patent: Nov. 2, 2010

(54) IMPLANTABLE CARDIAC DEVICE PROVIDING INTRINSIC CONDUCTION SEARCH WITH PREMATURE ATRIAL CONTRACTION PROTECTION AND METHOD

(75) Inventors: Jeff Zimmer, Nashville, TN (US); Diane Crawford, Hendersonville, TN (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 314 days.

(21) Appl. No.: 12/195,284

(22) Filed: Aug. 20, 2008

(65) Prior Publication Data
US 2008/0312710 A1    Dec. 18, 2008

Related U.S. Application Data

(63) Continuation of application No. 11/219,063, filed on Sep. 1, 2005, now Pat. No. 7,430,448.

(51) Int. Cl.
*A61N 1/362* (2006.01)
(52) U.S. Cl. .......................................... 607/9
(58) Field of Classification Search ............. 607/2, 607/9, 25
See application file for complete search history.

(56) References Cited

U.S. PATENT DOCUMENTS 5,623,936 A   4/1997   McClure
6,081,747 A   6/2000   Levine et al.
6,741,890 B1  5/2004   Seim et al.
6,745,075 B2  6/2004   Bjorling
7,072,714 B2  7/2006   Busch et al.
2003/0120165 A1  6/2003   Bjorling
2004/0215255 A1  10/2004  Vries

FOREIGN PATENT DOCUMENTS

EP    1321168 A2    6/2003

OTHER PUBLICATIONS

Levine, Paul A. MD et al., "Letters to the Editor," Pace. 2004;27:1691-1694.
Dennis, Malcolm J. et al., "Pacemaker Mediated Tachycardia as a Complication of the Autointrinsic Conduction Search Function," Pace. 2004;27(Pt. I):824-826.
NonFinal Office Action, mailed Nov. 5, 2007: Parent U.S. Appl. No. 11/219,063.
Final Office Action, mailed May 14, 2008: Parent U.S. Appl. No. 11/219,063.
Notice of Allowance, mailed Jul. 25, 2008: Parent U.S. Appl. No. 11/219,063.

*Primary Examiner*—Carl H Layno
*Assistant Examiner*—Brian T Gedeon

(57) ABSTRACT

The extended AV interval of an auto intrinsic conduction search of an implantable cardiac stimulation device has premature atrial contraction protection. A timer times a base AV interval and the extended AV interval. If the heart is paced with the extended AV interval and a premature atrial contraction is detected, the extended AV interval is maintained. Once a predetermined number of consecutive premature atrial contractions are detected, the extended AV interval is reset to the base AV interval.

7 Claims, 3 Drawing Sheets

IMPLANTABLE CARDIAC DEVICE PROVIDING INTRINSIC CONDUCTION SEARCH WITH PREMATURE ATRIAL CONTRACTION PROTECTION AND METHOD

CROSS REFERENCE TO RELATED APPLICATIONS

This application is a continuation of copending U.S. patent application Ser. No. 11/219,063, now U.S. Pat. No. 7,430,448 filed Sep. 1, 2005, titled "Implantable Cardiac Device Providing Intrinsic Conduction Search With Premature Atrial Contraction Protection And Method."

FIELD OF THE INVENTION

The present invention generally relates to an implantable cardiac device. The present invention more particularly relates to an implantable pacemaker capable of providing intrinsic conduction searching while also maintaining intrinsic conduction with respect to premature atrial contractions in combination with the intrinsic search algorithm.

BACKGROUND OF THE INVENTION

Implantable cardiac devices are well known in the art. They may take the form of implantable defibrillators or cardioverters which treat accelerated rhythms of the heart such as fibrillation. They may also take the form of implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

A popular mode of operation for dual-chamber pacemakers is the DDD mode. Specifically, DDD systems provide atrial pacing during atrial bradycardia, ventricle pacing in the setting of overt AV block or even compromised AV nodal conduction such as first degree AV block, and atrial and ventricular pacing during combined atrial and ventricular bradycardia or heart block also known as AV block. In addition, DDDR systems monitor patient activity levels for controlling pacing rate to more closely approximate the normal response of the heart to exercise, or other physiological activity demanding a faster heart rate.

Recent studies have indicated, however, that ventricular pacing in the setting of intact AV nodal conduction may have an adverse impact compared to permitting intrinsic ventricular contractions. Hence, pacing therapies have been advanced which encourage intrinsic ventricular activity while still providing back-up ventricular support should AV block develop. One such system employs an algorithm labeled auto intrinsic conduction search (AICS) wherein the pacemaker utilizes two AV intervals. The first interval is a programmable base AV interval to support ventricular demand pacing. It may be, for example, on the order of two hundred (200) milliseconds. The second AV interval is an extended AV interval which may be thought of as comprising the base AV interval with an AV interval extension added to its end. The AV interval extension may be on the order of one hundred (100) milliseconds, for example. Hence, in this example, the extended AV interval would be on the order of three hundred (300) milliseconds.

The AICS may be implemented as follows. Over a preset interval, for example five minutes, the device paces in a demand mode with the base AV interval. At the end of the preset or programmable time period, the algorithm extends the AV delay searching for intact AV nodal conduction. If a native QRS complex or "R wave" is detected during that extended AV delay, the extension remains in effect and the system functions as if it were a single chamber atrial pacemaker. The device does not reset to the shorter AV interval unless overt AV block occurs such that there is one cycle of AV pacing at the extended AV delay or the atrial rate exceeds a set upper atrial rate limit at which time the AV interval extension is canceled with the system returning to the programmed base AV delay. Following this, even if the rate slows below this set upper atrial rate limit, the programmed base AV delay remains in effect until the time-out occurs and a search for intrinsic conduction is again performed automatically by the algorithm. The upper atrial rate limit may be either preset on the order of ninety (90) beats per minute (bpm), for example or programmable.

Unfortunately, some patients with conduction delays at higher atrial rates run the risk of canceling the AICS feature if they have frequent premature atrial complex (PACs). A premature atrial complex is an atrial depolarization occurring early with respect to the basic sinus cycle. It is not unusual for a PAC to result in an effective atrial rate greater than the upper atrial rate limit for the atrial cycle in which it occurs. Hence, such an occurrence can run the risk of resetting the AICS extended AV interval to the base AV interval and reinitiate the five minute period of demand pacing at the shorter, base AV interval before a search is performed. This is indeed unfortunate because, PACs are generally isolated events although occasionally they can occur in short salvos. It would, of course, be desirable for patients with intact AV conduction who experience PACs to benefit from intrinsic ventricular activity and features such as AICS and not have this algorithm effectively canceled by transient non-sustained events.

SUMMARY

What is described herein is an implantable cardiac stimulation device comprising a pulse generator that provides pacing pulses on demand to a heart chamber upon time-out of an inhibit interval, and a timer that times a base inhibit interval and an extended inhibit interval. The device further comprises an intrinsic conduction control circuit that causes the timer to time the extended inhibit interval, a rate detector that detects a cardiac rate and causes the timer to time the base inhibit interval upon detecting a cardiac rate above a given rate, and a premature contraction detector that detects premature contractions of the heart and that overrides the rate detector from causing the timer to time the base inhibit interval upon detection of a premature contraction.

The premature contraction detector overrides the rate detector for a predetermined number of consecutive cardiac cycles in which the premature contraction detector detects a premature contraction. The pulse generator is preferably a dual chamber pulse generator and the inhibit interval may be an AV interval.

The rate detector may be an atrial rate detector. The premature contraction detector preferably detects premature atrial contractions. The atrial rate detector may include a timer that times atrial based intervals of consecutive cardiac cycles. The atrial based intervals may be intervals from a ventricular activation to a succeeding atrial activation. The atrial based intervals may alternatively be intervals between an atrial activation of one cardiac cycle and an atrial activation of a next succeeding cardiac cycle. The atrial rate interval may also be based on the ventricular rate from one ventricular event to the next ventricular event as long as each ventricular event is preceded by an atrial event at an appropriate AV delay.

The rate detector may cause the timer to time the base inhibit interval upon detecting a cardiac rate above the given rate and time-out of the extended inhibit interval.

In another embodiment, an implantable cardiac stimulation device comprises a pulse generator that provides pacing pulses on demand to a ventricle of a heart upon time-out of an AV interval, a timer that times a base AV interval and an extended AV interval, and an intrinsic conduction control circuit that causes the timer to time the extended AV interval when set and to time the base interval when reset. The device further comprises an atrial rate detector that detects an atrial rate above a given rate, a premature atrial contraction detector that detects premature atrial contractions of the heart, and a reset circuit that resets the intrinsic conduction control circuit responsive to the atrial rate detector detecting an atrial rate above the given rate in the absence of a detected premature atrial contraction and that maintains the intrinsic conduction control circuit in a set condition when the premature atrial contraction detector detects a premature atrial contraction of the heart notwithstanding a detected atrial rate above the given rate. The reset circuit resets the intrinsic conduction control circuit in response to a predetermined number of consecutive cardiac cycles in which the premature atrial contraction detector detects a premature atrial contraction.

The atrial rate detector may include a timer that times atrial based intervals of consecutive cardiac cycles. The premature atrial contraction detector may include a subtractor that subtracts a current atrial based interval from an immediately preceding atrial based interval to provide a difference, and a comparator that compares the difference to a predetermined standard to detect a premature atrial contraction.

The reset circuit may reset the intrinsic conduction control circuit whenever there is a time-out of the extended AV interval. The reset circuit may cause the timer to time the base AV interval for a cardiac cycle in which a premature atrial contraction is detected while maintaining the set condition.

In yet another embodiment, for use in an implantable cardiac stimulation device comprises providing pacing pulses on demand to a heart chamber upon time-out of an inhibit interval, providing a timer that times a base inhibit interval and an extended inhibit interval, and causing the timer to time the extended inhibit interval. The method further comprises detecting a cardiac rate above a given rate, causing the timer to time the base inhibit interval upon detecting a cardiac rate above the given rate, detecting premature contractions of the heart, and causing the timer to time the extended inhibit interval upon detection of a premature contraction notwithstanding detection of a cardiac rate above the given rate.

The step of causing the timer to time the base inhibit interval may be performed upon detecting a cardiac rate above the given rate and time-out of the extended inhibit interval. The timing of the extended inhibit interval may be performed for each one of a plurality of cardiac cycles in which a premature contraction is detected.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
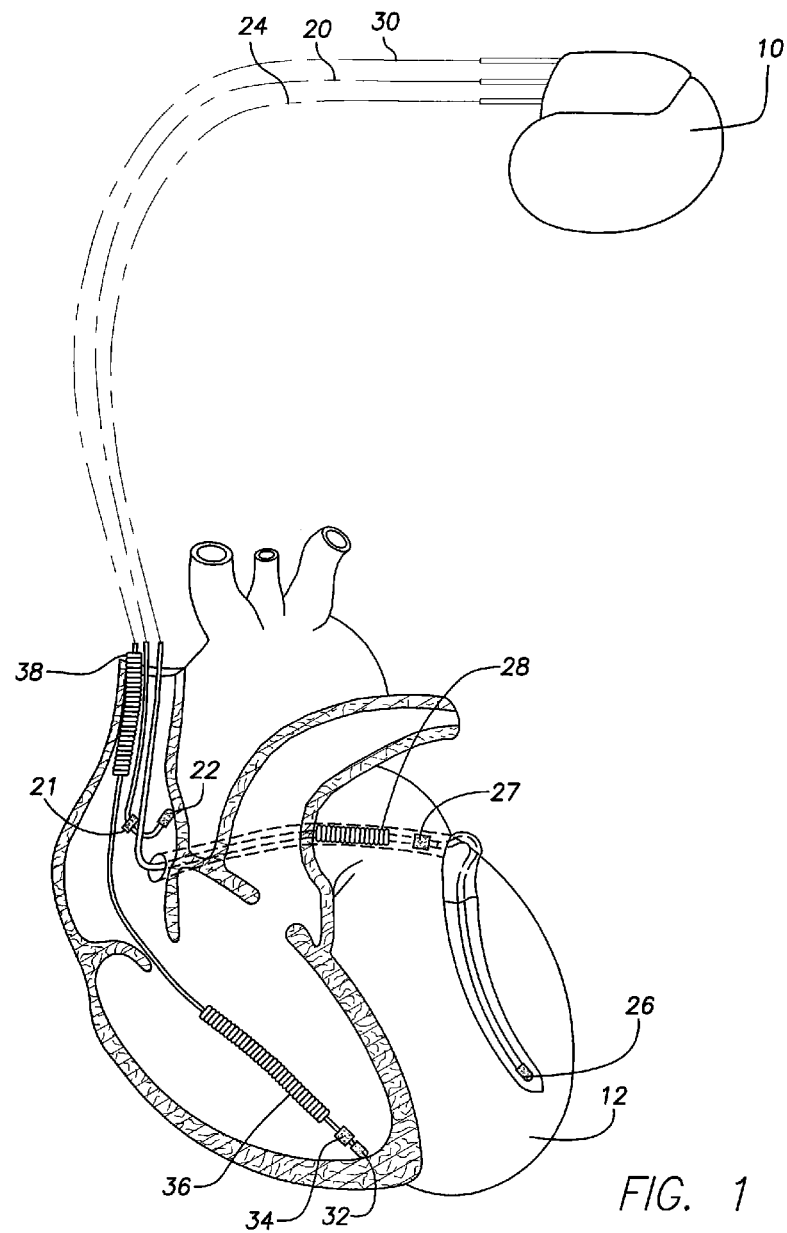
FIG. 1 is a simplified diagram illustrating an implantable stimulation device according to an embodiment of the present invention in electrical communication with a patient's heart.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. The coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
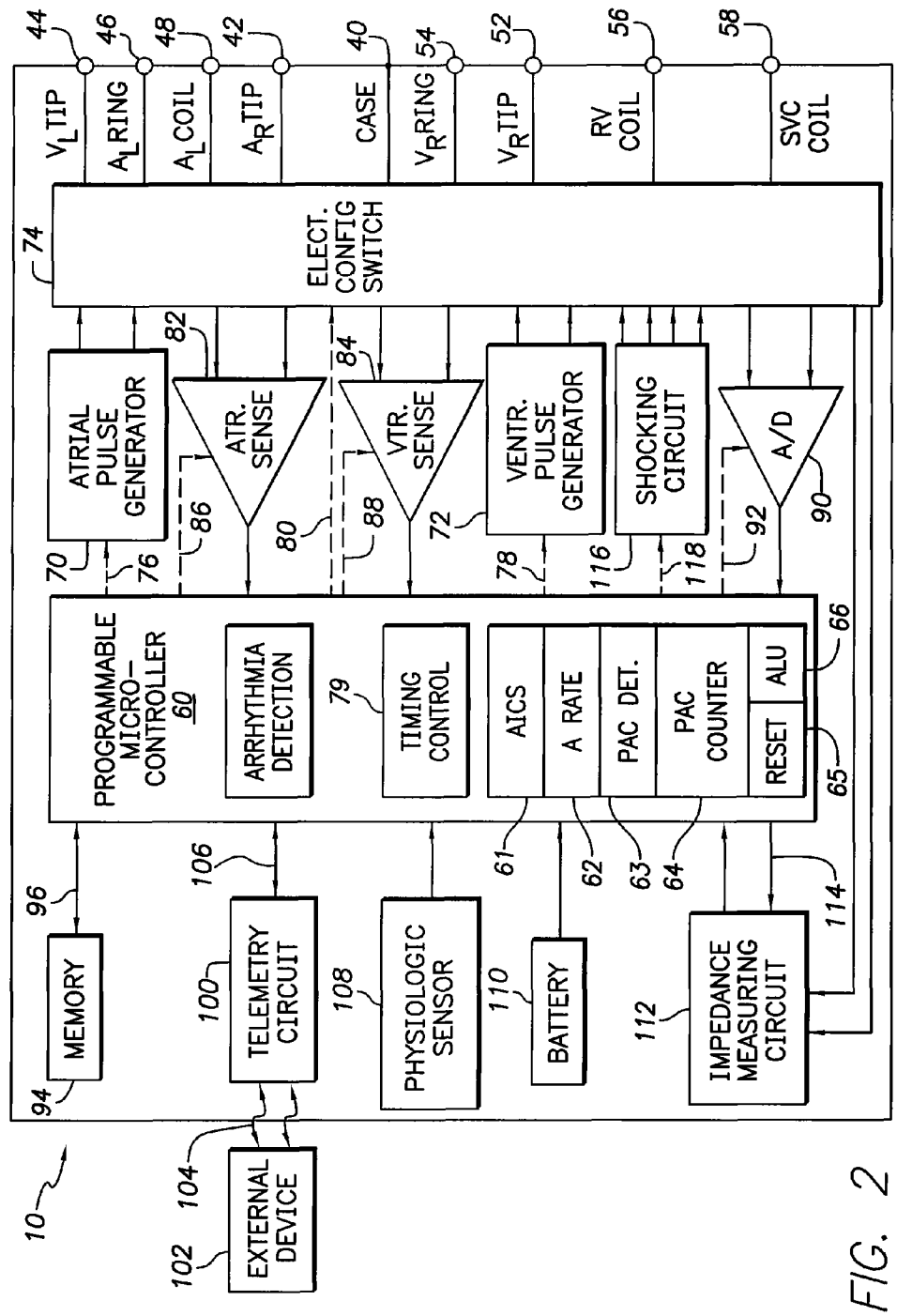
FIG. 2 is a functional block diagram of the implantable stimulation device of FIG. 1 according to an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79. The timing control circuitry 79 is used to control the timing of stimulation pulses (e.g., pacing rate, atrio-ventricular (AV) delay or intervals, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones)

and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level, and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

New that the device 10 has been generally described, this description will now continue by describing those elements of the device 10 which are more particularly employed in this embodiment of the present invention. To that end, it may be noted that the device 10 further includes an auto intrinsic conduction search (AICS) circuit 61, an atrial rate detector 62, a PAC detector 63, a PAC counter 64, a reset circuit 65, and an ALU circuit 66. As shown, each of these circuits is implemented by the microcontroller 60 but, as may be appreciated by those skilled in the art, may alternatively be implemented with discrete circuitry.

The AICS circuit 61 may function as previously described to encourage intrinsic ventricular activity. Hence, it may cause the timing control 79 to time the extended AV interval when active to encourage intrinsic ventricular activity and be reset to cause the timing control to time the shorter base AV interval.

The atrial rate detector 62 preferably times atrial based intervals. The atrial based intervals may be the time between R waves and P waves/A waves. Alternatively, the atrial based intervals may be the time between an atrial activation (A wave or P wave) of one cardiac cycle and an atrial activation (A wave or P wave) of the next cardiac cycle. The atrial based intervals may be the time between consecutive R waves (or V-R intervals) as long as each ventricular event is preceded by an atrial event.

The PAC detector may use the atrial based intervals timed by the atrial rate detector 62 to detect PACs. This may be accomplished by subtracting the previously R to P/A or P/A to P/A interval from a current R to P or P/A to P interval to determine a difference ($\Delta$). The difference may then be compared to a predetermined standard, such as, for example, 50 ms to 150 ms cycle to cycle variation. If the difference in absolute intervals (ms) is greater than the predetermined standard, detection of a PAC is declared. A PAC may also be determined using percentages if R to P or P/A to P interval is shorter than the base interval by a specified percentage.

If the difference is not less than the predetermined standard, the AICS will not receive PAC protection treatment. In this setting, if the atrial rate is above the upper atrial rate limit or if there is an extended AV interval time-out and a ventricular pacing be issued, the AICS AV interval will be reset to the base interval. This will then follow the standard algorithm behavior for AICS.

The PAC counter 64, as will be seen subsequently keeps track of the number of consecutive PACs. This is performed because the PAC AICS protection may be desired for each one of a predetermined number of consecutive PACs. When the predetermined number of consecutive PACs occur, the AICS AV interval will be reset. Hence, if one PAC is to be tolerated without an AICS AV interval reset, the predetermined number would be two. If X consecutive PACs are to be tolerated, then the predetermined number would be X+1.

The reset circuit 65 resets the AICS AV interval. It may take input from the PAC detector 63, the atrial rate detector 62, the timing control 79, and the PA counter. If the PAC is detected, the reset circuit 65 will not reset the AICS AV interval unless the predetermined number of consecutive PACs have been reached. If the predetermined number of PACs has been reached, reset circuit will reset the AV interval to the base interval.

If the reset circuit 65 receives input from the atrial rate detector that the atrial rate is above the upper atrial rate and there is no PAC, the reset circuit 65 will reset the AICS AV interval to the base interval. The AV interval will also be reset whenever there is a time-out of the extended AV interval and a ventricular pacing pulse is issued.

The ALU 66 is provided to process required arithmetic functions. For example, the ALU 66 may be called upon to function as a subtractor for calculating the difference ($\Delta$). It may also be used for division for calculating cardiac rates based upon cardiac intervals.

Figure 3:
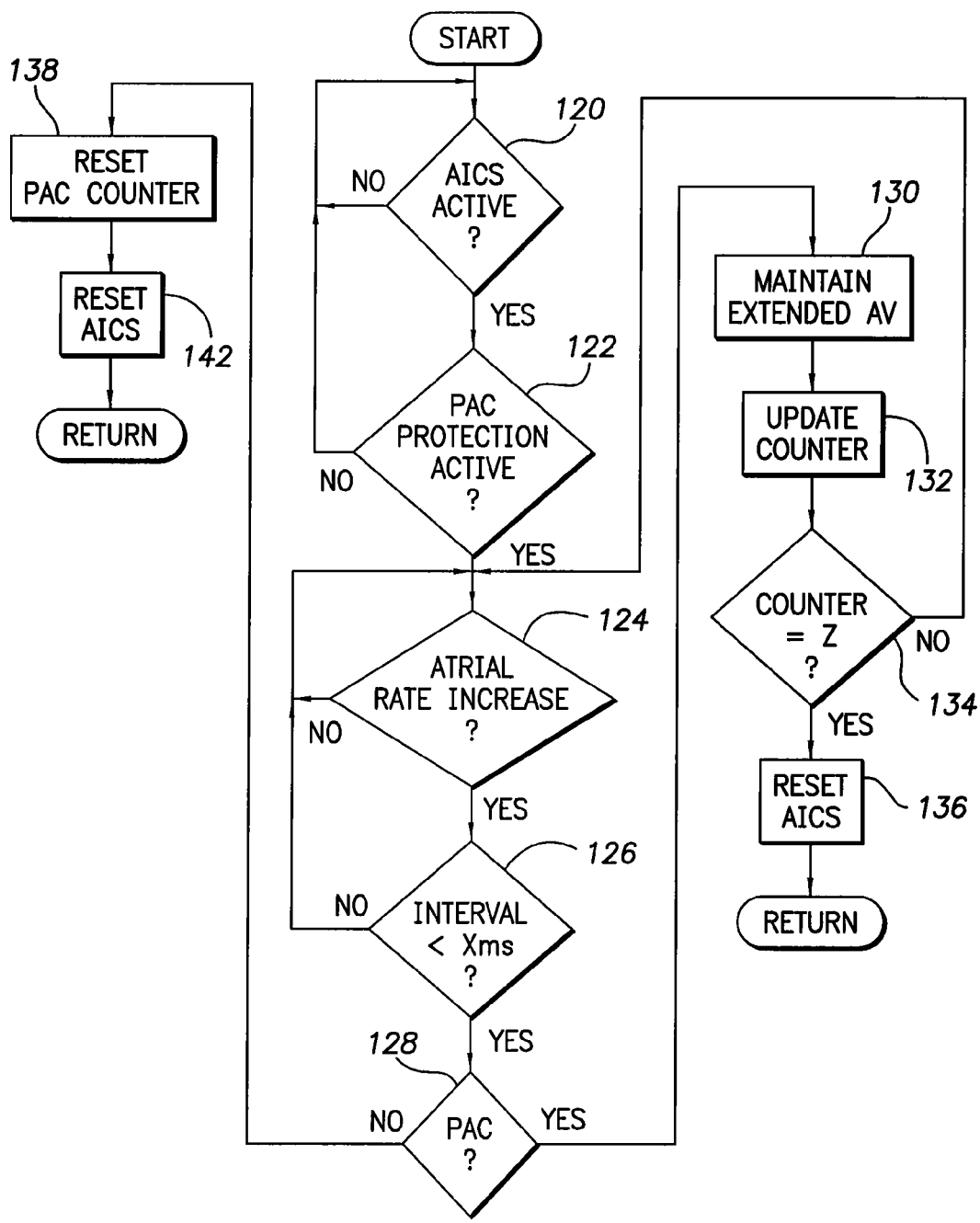
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 is more particularly directed to providing the AICS 61 with PAC protection and resetting the AICS extended AV interval to the base AV interval which then begins again a period in which intrinsic conduction is analyzed before the extended AV interval is once again reinstated. It is to be understood that, in this embodiment, whenever there is a time-out of the extended AV interval that the AICS is reset reinstating the base AV interval.

The process of FIG. 3 initiates with decision block 120. Here, it is determined if the auto intrinsic conduction search circuit 61 is active (set). If it is not active, the process returns. However, if the AICS is active, the process then advances to decision block 122. In decision block 122, it is determined if the premature atrial contraction protection for the AICS process is active. If it is not, the process returns. However, if the PAC protection is active, the process advances to decision block 124.

In decision block 124, it is determined if there is an atrial rate increase. Decision block 124 may be implemented by comparing the atrial-based interval of the current cardiac cycle with the atrial-based interval of the immediately preceding cardiac cycle. If the atrial-based interval of the current cardiac cycle is shorter than the atrial-based interval of the previous cardiac cycle, an atrial rate increase will be declared and the process advances to decision block 126. If an atrial rate increase is not declared, the process then returns to look for an atrial rate increase during the next cardiac cycle.

In decision block 126, it is determined if the interval is shorter than a particular interval of X milliseconds. The interval of X milliseconds is chosen so as to represent the upper atrial rate minimum interval. As previously described, the upper atrial rate may be 90 beats per minute (bpm). This would correspond to a minimum interval of 666 milliseconds. If the upper atrial rate limit is 90 bpm, it is determined in decision block 126 if the last atrial interval is less than 666 milliseconds. If it is not, the process returns to decision block 124. However, if it is, the process advances to decision block 128 to determine if the atrial rate above the upper atrial limit for the current cardiac cycle resulted from a premature atrial contraction. The presence of a PAC may be determined as previously described by subtracting an atrial-based interval of the current cycle from the atrial-based interval of the immediately preceding cardiac cycle to determine a difference and then comparing that difference to a predetermined standard between 50 to 150 milliseconds, for example. If the difference is greater than the predetermined standard, the detection of a PAC will be declared. However, if the difference is less than a predetermined standard, the detection of a PAC will not be declared.

Those skilled in the art will appreciate that there are a number of different ways in which a PAC may be detected. For example, a PAC may be detected by monitoring A to A or V to V intervals and if a native complex occurs that is more premature based upon a percentage of the preceding cycle length, detection of a PAC may be declared. Other methodologies for detecting PACs are also available. Hence, it is to be understood, that the particular method of detecting PACs described herein is exemplary only.

If a PAC is detected in accordance with decision block 128, the process advances to activity block 130 wherein any attempt to reset the AICS AV interval to the base interval is overridden to maintain the extended AV interval. Hence, the reset circuit 65 does not cause the AICS circuit 61 to in turn cause the timing control 79 to start timing the base AV interval. Next, the process advances to activity block 132 where the PAC counter 64 is updated. The PAC counter 64 will now have the most recent consecutive number of detected PACs since the last AICS AV interval reset. After activity block 132, the process advances to decision block 134, wherein it is determined if the count in the PAC counter 64 is equal to the predetermined number. If it is, indicating that the predetermined number of PACs have occurred while the AICS is active, the process advances to activity block 136 for resetting the AV interval of the AICS to the base interval for the next cardiac cycle and to initiate the period in which the AICS evaluates the intrinsic conduction of the patient. As previously described, if one PAC is to be tolerated, then the predetermined number to which the counter is compared in decision block 134 would be 2. If the number of consecutive PACs to be tolerated is 2 PACs, the predetermined number to which the PAC counter count is compared in decision block 134 is 3, and so on. If in decision block 134 it is determined that the PAC counter count is not equal to a predetermined number, a process returns to decision block 124 to assess the next cardiac cycle for an atrial rate increase. Following reset of the AV interval in activity block 136, the process returns.

Returning now to decision block 128, if in decision block 128 it is determined that a PAC has not been detected, the process advances to activity block 138 wherein the PAC counter 64 is reset. The non-detection of a PAC in decision block 128 breaks the consecutive chain of PAC detections.

At this point in the process, a PAC has not been detected but an atrial rate greater than the upper atrial rate has been detected. In this event, the process advances to activity block 142 wherein the AV interval of the AICS is reset to the base interval to initiate the period of intrinsic conduction analysis. Following activity block 142, the process returns.

Hence, as may be seen from the foregoing, intrinsic conduction of a patient is encouraged by the AICS process. The AICS process has protection from premature atrial contractions. Hence, a premature atrial contraction while the AICS is causing the timing control 79 to time the extended AV interval will not cause the AV interval to be reset to the base AV interval. The process is arranged to tolerate a number of consecutive PACs without resetting the AV interval to the base interval. In addition, whenever there has been an AV time-out of the extended AV interval and a ventricular pacing pulse issued, the AICS is reset to reinstate the base AV interval. In another implementation, the device may recognize a PAC and the effective PAC rate may exceed the rate cutoff for the AICS algorithm. For the PAC complex only, the system may return to the programmed base AV delay but, because this is in response to a PAC, the AICS extension is not suspended. On the next cycle, in which a normal sinus complex occurs at a rate below the rate cutoff, the AICS extension will still be in effect allowing for appropriate inhibition of the ventricular channel. Hence, activity block 130 of FIG. 3 may be modified to cause the timer 79 to time the base AV interval for the current cardiac cycle (the PAC cycle) while maintaining the set condition of the AICS 61.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   one or more electrodes adapted for coupling with cardiac tissue;
   a pulse generator adapted to output pacing pulses to the electrodes;
   a converter adapted to sense cardiac polarizations through the electrodes; and
   a controller coupled to the pulse generator and the converter and having code stored therein that defines a base inhibit interval and an extended inhibit interval, the controller programmed to:
   periodically control the pulse generator to deliver pacing pulses upon expiration of the extended inhibit interval while processing the cardiac polarizations sensed by the converter to determine if the cardiac rate has increased by a threshold amount and if the cardiac rate has increased by a threshold amount, to detect for premature contractions;
   control the pulse generator to deliver pacing pulses upon expiration of the base inhibit interval if the cardiac rate has increased by a threshold amount and no premature contractions are detected; and
   control the pulse generator to deliver pacing pulses upon expiration of the extended inhibit interval if the cardiac rate has increased by a threshold amount and one or more premature contractions are detected.

2. The device of claim 1 wherein the cardiac polarizations sensed by the converter comprise atrial polarizations and the cardiac rate is based on consecutive atrial polarizations.

3. The device of claim 1 wherein the cardiac polarizations sensed by the converter comprise atrial polarizations and ventricular polarizations and the cardiac rate is based on intervals from a ventricular polarization to a succeeding atrial polarization.

4. The device of claim 1 wherein the pulse generator is a ventricular pulse generator and the inhibit interval is an atrio-ventricular (AV) interval.

5. The device of claim 1 wherein if the cardiac rate has increased by a threshold amount and one or more premature contractions are detected, the controller is further programmed to maintain a count of detected premature contractions and control the pulse generator to deliver pacing pulses upon expiration of the base inhibit interval after the premature contractions count exceeds a predetermined number.

6. The device of claim 1 wherein the premature contractions comprise premature atrial contractions (PACs).

7. The device of claim 6 wherein the controller is programmed to detect PACs by:
   subtracting a current atrial based interval from an immediately preceding atrial based interval to provide a difference; and
   comparing the difference to a predetermined standard to detect a premature atrial contraction.

* * * * *